United States Patent [19]

Hu

[11] Patent Number: 6,132,740
[45] Date of Patent: *Oct. 17, 2000

[54] RESORCINOL DERIVATIVES

[75] Inventor: Lan Hu, Dix Hills, N.Y.

[73] Assignee: Pfizer Inc., New York, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 09/153,479

[22] Filed: Sep. 15, 1998

Related U.S. Application Data

[60] Provisional application No. 60/059,625, Sep. 23, 1997.

[51] Int. Cl.$^7$ .................. A61K 6/00; A61K 7/00
[52] U.S. Cl. .................. 424/401; 424/59; 424/60; 424/62; 514/730; 514/731; 514/732; 514/733; 514/844
[58] Field of Search ............... 424/401, 59, 60, 424/62; 514/730, 731, 732, 733, 844

[56] References Cited

U.S. PATENT DOCUMENTS

| | | | |
|---|---|---|---|
| 3,697,275 | 10/1972 | Hayakawa et al. | 96/48 |
| 3,756,818 | 9/1973 | Hayakawa et al. | 96/48 |
| 3,933,925 | 1/1976 | Greco | 260/621 |
| 4,006,218 | 2/1977 | Sipos | 424/54 |
| 4,225,619 | 9/1980 | Brickl et al. | 424/331 |
| 4,391,827 | 7/1983 | Harbert et al. | 424/331 |
| 5,304,679 | 4/1994 | McEvily et al. | 564/158 |
| 5,399,785 | 3/1995 | Miura et al. | 568/766 |
| 5,449,518 | 9/1995 | Junino et al. | 424/401 |
| 5,468,472 | 11/1995 | LaGrange et al. | 424/62 |

FOREIGN PATENT DOCUMENTS

| | | |
|---|---|---|
| 2094465 | 10/1993 | Canada . |
| 0341664 | 11/1989 | European Pat. Off. . |
| 0524439 | 1/1993 | European Pat. Off. . |
| 0551849 | 7/1993 | European Pat. Off. . |
| 0623339 | 11/1994 | European Pat. Off. . |
| 0701988 | 3/1996 | European Pat. Off. . |
| 3127590 | 8/1982 | Germany . |
| 3604865 | 8/1987 | Germany . |
| 0249715 | 2/1990 | Japan . |
| 4169511 | 6/1992 | Japan . |
| 4169516 | 6/1992 | Japan . |
| 0054905 | 1/1993 | Japan . |
| 0656641 | 3/1994 | Japan . |
| 9013618 | 11/1990 | WIPO . |
| 9111119 | 8/1991 | WIPO . |

OTHER PUBLICATIONS

McEvily, A.J. et al., Inhibition of Polyphenol Oxidase by Phenolic Compounds, ACS Symp. Service, 318–25, 1992.
Yusupov et al., 1970, Uzbek Chemical Journal 14(5):66–69, "Reaction of resorcinol and its methyl esters with cyclopentene and cyclohexene." (with complete English translation).
Ardurasuleva et al., 1968, Uzbek Chemical Journal 12(5):37–41, "Cyclopentylation of resorcinol and its esters." (with complete English translation).
Yusopov et al., 1970 Uzbek SSR Academy of Sciences 27(6):38–39, "Cycloalkylation of resorcinol and its esters" (with complete English translation).
Baek, 1988, Bull. Korean Chem. Soc. 9:71–77, "A simple one–step alkylation of orcinol derivatives".
Baek, 1994, J. Chem. Res. (S), 451, Simplified cannabidiols, Part 1, Boron trifluoride–diethyl ether on alumina.
Fujikawa et al., 1972, Yakugaku Zasshi 92:768–71, "Studies on antiseptics for foodstuff. LXXIII". (Japanese article with English abstract).
Gottesfeld et al., 1971, Biochim. Biophys.Acta 228:365–381, "The inhibition of deoxyribonuclease I by hydroxybiphenyls".
Pisanenko et al., 1976, Khim.–Farm. Zh. 10:35–36, "Antimicrobial activity of cycloalkenyl– and 4–(α–aryl cyclopentyl)–phenols" (Russian article with English translation).
Repinskaya et al., 1980, Zh. Organ. Khim., 16:1508–1514, "Reaction of phenols and their derivatives with aromatic compounds in the presence of acidic agents".
Yamazaki, 1954, CA 51:1464h.
Sakai et al., 1956, CA 51:531Oe.
Fushimi, 1956, CA 51:13219b.
Ashikaga, 1954, CA 52:10391i.
Deorha et al., 1965, CA 63:6872g.

*Primary Examiner*—Jose' G. Dees
*Assistant Examiner*—Michael A. Williamson
*Attorney, Agent, or Firm*—Peter C. Richardson; Paul H. Ginsburg; Alan L. Koller

[57] ABSTRACT

The present invention relates to the use of certain resorcinol derivatives as skin lightening agents.

35 Claims, No Drawings

RESORCINOL DERIVATIVES

This application claims priority under 35 U.S.C. § 119(e) from U.S. provisional application Serial No. 60/059,625, filed Sep. 23, 1997.

The present invention relates to the use of certain resorcinol derivatives as skin lightening agents.

The terms "lightening agent" and "depigmentation agent" are used interchangeably throughout this document.

Skin color in humans arises from a complex series of cellular processes which are carried out within a unique population of cells called melanocytes. Melanocytes are located in the lower part of the epidermis, and their function is to synthesize a pigment, melanin, which protects the body from the damaging effects of ultraviolet radiation.

When skin is exposed to ultraviolet radiation, such as that contained in sunlight, melanocytes increase their synthesis of melanin. Melanin is deposited in melanosomes, which are vesicles found within the cell. The melanosomes are extruded from the cell and carried to the surface of the skin by keratinocytes, which internalize the melanin containing melanosomes. The end result is that the visible layers of the skin exhibit a brown color typically known as a "tan". The darkness of the color observed in the skin is proportionate to the amount of melanin synthesized by melanocytes and transferred to the keratinocytes.

The mechanism by which skin pigmentation is formed, melanogenesis, is particularly complex and schematically involves the following main steps: Tyrosine→L-Dopa→Dopaquinone→Dopachrome→Melanins. The first two reactions in this series are catalyzed by the enzyme tyrosinase. The activity of tyrosinase is promoted by the action of α-melanocyte stimulating hormone or UV rays to have melanin eventually formed as chromatism in the skin. It is well established that a substance has a depigmenting effect if it acts directly on the vitality of the epidermal melanocytes where melanogenesis normally occurs and/or if it interferes with one of the stages in melanin biosynthesis. The active compounds that are employed in the various methods and compositions of this invention inhibit tyrosinase and thus inhibit or decrease melanin biosynthesis.

There is a strong demand for agents which enable acquired deposition sites, such as spots or freckles, to be restored to a normal skin color. For this purpose, a variety of agents and methods have been developed and put on the market. Examples of such methods are (a) a method wherein vitamin C (L-ascorbic acid) having good reducing ability is administered orally in large amounts, (b) a method wherein glutathione is administered parenterally; (c) a method wherein a peroxide, such as hydrogen peroxide, zinc peroxide, sodium peroxide and the like, which is believed to have the bleaching action of melamine, is administered: and (d) a method wherein vitamin C or cysteine is administered topically in the form of an ointment, cream, lotion or the like. Vitamin C has a problem with respect to stability and becomes so unstable in water-containing systems that they will cause changes in odor and color. Thiol compounds such as glutathione and cysteine do not exhibit a satisfactory depigmental effect since the development of the effect is very slow.

The substances in widest use at the present time as depigmentors are, in particular, hydroquinone and its derivatives, particularly its ethers such as hydroquinone monomethyl ether. These compounds, while effective, are known to produce side effects, that can be dangerous. Hydroquinone, use of which is limited to a concentration of 2%, is both irritating and cytotoxic to the melanocyte.

U.S. Pat. No. 4,526,179 refers to certain hydroquinone fatty esters that have good activity and are less irritating and more stable than hydroquinone.

Japanese Patent Application No. 27909/86 refers to other hydroquinone derivatives that do not have the drawbacks of hydroquinone but that have relatively poor efficacy.

U.S. Pat. No. 5,449,518 refers to 2,5-dihydoxyphenyl carboxylic acid derivatives as skin depigmentation agents.

European Patent Application EP 341,664A1 refers to certain resorcinol derivatives as tyrosinase inhibitors and skin depigmentation agents.

The use of topical depigmentation agents that have good efficacy and are harmless is particularly desirable for treating the following: regional hyperpigmentation caused by melanocytic hyperactivity, such as idiopathic melasma occurring either during pregnancy (mask of pregnancy or chloasma) or secondary to estrogen-progesterone contraception; local hyperpigmentation caused by benign melanocytic hyperactivity and proliferation such as lentigo senilis or liver spots; accidental hyperpigmentation such as postlesional photosensitization and scarring; and certain forms of leukoderma such as vitiligo where, if the injured skin cannot be repigmented, the residual zones of normal skin are depigmented to impart a homogeneous white color to the entire skin.

The resorcinol derivatives of formula I, which are defined below and used in the various methods and compositions of this invention, are useful in the treatment of the foregoing dermatological conditions as well as other dermatological conditions, some of which are referred to later in this document, for which the subject being treated desires, for medicinal or cosmetic purposes, to lighten or reduce the pigmentation of the skin affected by the condition.

The resorcinol derivatives of formula I are also useful for the treatment of inflammatory disorders such as psoriasis and acne.

SUMMARY OF INVENTION

The invention relates to the use of 4-cycloalkyl resorcinols having the formula:

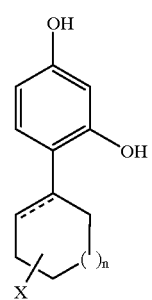

I wherein X is hydrogen; $OR^1$, wherein $R^1$ represents hydrogen, $(C_1-C_6)$alkyl or aryl-$(C_1-C_6)$alkyl; $OCOR^2$ wherein $R^2$ represents $(C_1-C_6)$alkyl, aryl-$(C_1-C_6)$alkyl or phenyl; halogen; $(C_1-C_6)$alkyl; aryl-$(C_1-C_6)$alkyl; $SR^3$ wherein $R^3$ represents hydrogen, $(C_1-C_6)$alkyl, or aryl-$(C_1-C_6)$alkyl; or $NHR^1$ wherein $R^1$ is defined as above;

n is 0 to 3; and the dashed line indicates an optional double bond at that position.

The present invention also relates to the pharmaceutically acceptable acid addition and base salts of compounds of the formula I. The acids which are used to prepare the pharmaceutically acceptable acid addition salts of the aforementioned base compounds of this invention are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1-methylene-bis-(2-hydroxy-3-naphthoate)] salts.

The term "alkyl", as used herein, unless otherwise indicated, includes saturated monovalent hydrocarbon radicals having straight, branched or cyclic moieties or combinations thereof.

The term "aryl", as used herein, refers to phenyl or naphthyl optionally substituted with one or more substituents, preferably from zero to two substituents, independently selected from halogen, $(C_1-C_6)$alkyl, $(C_1-C_6)$alkoxy, amino, $(C_1-C_6)$alkylamino, di-$[(C_1-C_6)$alkyl$)]$amino, nitro, cyano and trifluoromethyl.

The term "one or more substituents", as used herein, refers to a number of substituents that equals from one to the maximum number of substituents possible based on the number of available bonding sites.

The "halogen", as used herein, unless otherwise indicated, include chloro, fluoro, bromo and iodo.

Examples of more specific embodiments of the present invention include:

(a) compounds of the formula I wherein a single bond connects the two carbon atoms at the dashed line;

(b) compounds of the formula I wherein n is one;

(c) compounds of the formula I wherein X is hydrogen;

(d) compounds of the formula I wherein X is hydrogen, methyl or ethyl;

(e) compounds of the formula I wherein n is zero;

(f) compounds of the formula I wherein n is two; and (g) compounds of the formula I wherein X is benzyloxy.

In a preferred embodiment, the compound of formula I is 4-cyclohexylresorcinol or 4-cyclopentylresorcinol.

The present invention also relates to a topical pharmaceutical composition for lightening skin or reducing the pigmentation of skin in a human, comprising an amount of a compound of the formula I, or a pharmaceutically acceptable salt thereof, that is effective in lightening skin or reducing the pigmentation of the skin, and a pharmaceutically acceptable carrier.

The present invention also relates to a method of lightening skin or reducing the pigmentation of skin in a human, comprising administering to said human an amount of a compound of the formula I, or a pharmaceutically acceptable salt thereof, that is effective in lightening skin or reducing the pigmentation of skin.

The present invention also relates to a topical pharmaceutical composition for inhibiting tyrosinase in a human, comprising a tyrosinase inhibiting effective amount of a compound of the formula I, or a pharmaceutically acceptable salt thereof, and a pharmaceutically acceptable carrier.

The present invention also relates to a method of inhibiting tyrosinase in a human, comprising administering to said mammal a tyrosinase inhibiting effective amount of a compound of the formula I, or a pharmaceutically acceptable salt thereof.

The present invention also relates to a topical pharmaceutical composition for lightening skin or reducing the pigmentation of skin in a human, comprising a tyrosinase inhibiting effective amount of a compound of the formula I, or a pharmaceutically acceptable salt thereof, and a pharmaceutically acceptable carrier.

The present invention also relates to a method of lightening skin or reducing the pigmentation of skin in a human, comprising administering to said human a tyrosinase inhibiting effective amount of a compound of the formula I, or a pharmaceutically acceptable salt thereof.

The present invention also relates to a topical or transdermal pharmaceutical composition for the treatment of an inflammatory disorder such as acne or psoriasis in a human, comprising an amount of a compound of the formula I, or a pharmaceutically acceptable salt thereof, that is effective in treating such disorder, and a pharmaceutically acceptable carrier.

The present invention also relates to a method of treating inflammatory disorders such as psoriasis and acne in a human, comprising administering to said human an amount of a compound of the formula I, or a pharmaceutically acceptable salt thereof, that is effective in treating such disorder.

The present invention also relates to a topical or transdermal pharmaceutical composition for the treatment of an inflammatory disorder such as acne or psoriasis in a human, comprising a tyrosinase inhibiting effective amount of a compound of the formula I, or a pharmaceutically acceptable salt thereof, and a pharmaceutically acceptable carrier.

The present invention also relates to a method of treating inflammatory disorders such as psoriasis and acne in a human, comprising administering to said human a tyrosinase inhibiting effective amount of a compound of the formula I, or a pharmaceutically acceptable salt thereof.

Compounds of formula I may contain chiral centers and therefore may exist in different enantiomeric and diastereomeric forms. This invention relates to all optical isomers and all stereoisomers of compounds of the formula I and mixtures thereof, and to all pharmaceutical compositions and methods of treatment defined above that contain or employ them, respectively.

Formula I above includes compounds identical to those depicted but for the fact that one or more hydrogen, carbon or other atoms are replaced by isotopes thereof. Such compounds may be useful as research and diagnostic tools in metabolism pharmacokinetic studies and in binding assays.

DETAILED DESCRIPTION OF THE INVENTION

The compounds of the formula I may be prepared as described in the following reaction schemes and discussion. Unless otherwise indicated, X, n, $R^1$, $R^2$ and $R^3$ and structural formula I in the reaction schemes and discussion that follow are defined as above.

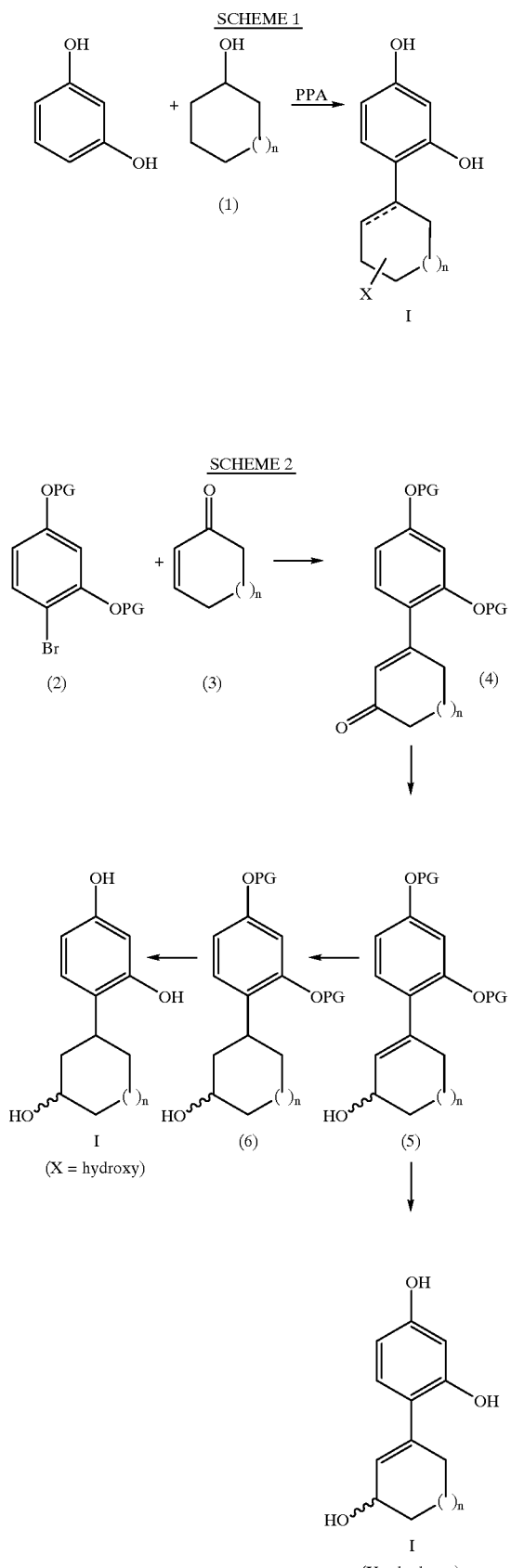

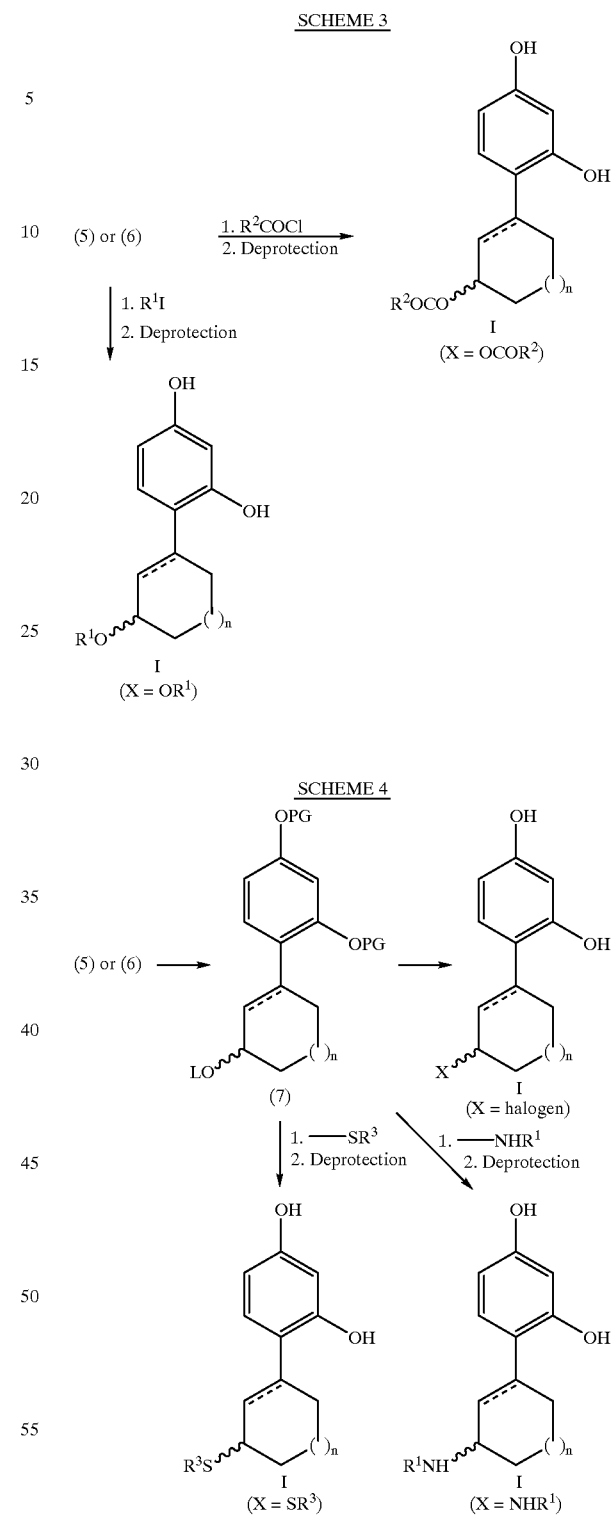

Reaction schemes 1 through 4 illustrate various methods of synthesizing compounds of the formula I.

Referring to Scheme 1, compounds of the formula I can be formed by heating resorcinol with the appropriate cycloalkanol of formula (1) using polyphosphoric acid (PPA) or another suitable acidic catalyst. When PPA is used, the reaction is typically carried out using one to three equivalents of the alcohol in neat PPA at a temperature between about 100° C. and about 160° C.

Referring to Scheme 2, the starting material of formula (2) can be obtained by protecting commercially available 4-bromoresorcinol. Suitable protecting groups (PG) are methyl ($CH_3$) and benzyl ($CH_2C_6H_5$), and can be introduced by conventional methods that are well known to those of skill in the art. For example, the methyl and benzyl protected compounds may be obtained by alkylating 4-bromoresorcinol with two equivalents of methyl iodide or benzyl bromide, respectively, and five equivalents of potassium carbonate in an acetone solvent at about room temperature.

Compounds of the general formula (3) are known and may be obtained using conventional methods well known to those of skill in the art. Compounds of the formula (4) can be obtained by reaction of compounds of the formula (2) and those of the formula (3) under Heck conditions. Specifically, the Heck reaction may be carried out using palladium (II) acetate (one mole percent), triphenylphosphine (two mole percent) and triethylamine (one equivalent), and heating the reaction mixture in a suitable solvent (e.g., N,N-dimethylformamide (DMF)) at a temperature from about 80° C. to about 130° C. Reduction of compounds of the formula (4) with di(isobutyl)aluminum hydride (DIBAL-H) gives the corresponding allylic alcohols of formula (5). Hydrogenolysis of alcohols of formula (5), for example, using hydrogen gas and a metal catalyst such as palladium-on-charcoal in ethanol at about room temperature, yields the saturated analogues of formula (6), which can then be deprotected under suitable conditions to give the correspondent resorcinols of formula I wherein X is hydroxy. Alternatively, similar deprotection of the allylic alcohols of formula (5) yields the corresponding resorcinols of formula I wherein X is hydroxy.

Referring to Scheme 3, esterification of compounds of the formula (5) or (6) with an appropriate acyl chloride ($R^2COCl$) under conventional conditions well known to those of skill in the art, followed by suitable deprotection, gives the corresponding compounds of formula I wherein X is $OCOR^2$. For example, esterification can be accomplished by reacting the alcohol of formula (5) or (6) with one equivalent of an acyl chloride and one equivalent of triethylamine in dichloromethane at about room temperature. Alkylation of compounds of the formula (5) or (6) with an alkyl iodide ($R^1I$) in the presence of base (using, for example, one equivalent of sodium hydride and the desired alkylating agent in the form of an alkyl chloride, bromide or iodide, in tetrahydrofuran (THF) at about the reflux temperature), using methods well known to those of skill in the art, followed by deprotection, gives the corresponding compounds of the formula I wherein X is $OR^1$.

Referring to Scheme 4, transformation of the alcohol function in compounds of the formula (5) or (6) into a suitable leaving group (L), such as, for example, mesylate, gives the corresponding compounds of formula (7). Formation of the mesylate may be carried out using one equivalent of mesyl chloride and one equivalent of triethylamine in dichloromethane at about room temperature. Displacement with a thioalkoxide (for example, by reacting the compound of formula (7) with the appropriate lithium or sodium thioalkoxide in THF at the reflux temperature), and subsequent deprotection using conventional methods well known to those skilled in the art, leads to the corresponding compounds of formula I wherein X is $SR^3$. Alternatively, displacement with an amine, for example, by reacting the compound of formula (7) with one equivalent of the appropriate amine of the formula $R^1NH_2$ in THF at the reflux temperature, followed by deprotection, yields the corresponding compounds of the formula 1 wherein X is $NHR^1$.

Compounds of the formula I wherein X is halogen can be obtained from the corresponding compounds of formula (7) by displacement with the appropriate metal halide and subsequent deprotection using conventional methods well known to those of skill in the art.

The compounds of formula I that are basic in nature are capable of forming a wide variety of different salts with various inorganic and organic acids. Although such salts must be pharmaceutically acceptable for administration to animals, it is often desirable in practice to initially isolate a compound of the formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the active base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of formula I that are acidic in nature are capable of forming base salts with various pharmaceutically acceptable cations. Examples of such salts include the alkali metal and alkaline earth metal salts and, particularly, the sodium and potassium salts. These salts can be prepared by conventional techniques. The chemical bases that are used as reagents to prepare the pharmaceutically acceptable base salts of this invention are those that form non-toxic base salts with the acidic compounds of formula I. Such non-toxic base salts include those derived from such pharmaceutically acceptable cations as sodium, potassium, calcium and magnesium, etc. These salts can easily be prepared by treating the corresponding acidic compounds with an aqueous solution containing the desired pharmaceutically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness, as described above. In either case, stoichiometric quantities of reagents are preferably employed in order to ensure completeness of reaction and maximum yields of the desired final products.

Compounds of the formula I and their pharmaceutically acceptable salts (hereinafter "the active compounds used in this invention") are useful in the treatment of disorders of human pigmentation, including solar and simple lentigines (including age/liver spots), melasma/chloasma and postinflammatory hyperpigmentation. Such compounds reduce skin melanin levels by inhibiting the production of melanin, whether the latter is produced constitutively or in response to UV irradiation (such as sun exposure). Thus, the active compounds used in this invention can be used to reduce skin melanin content in non-pathological states so as to induce a lighter skin tone, as desired by the user. They can also be used in combination with skin peeling agents (including glycolic acid or trichloroacetic acid face peels) to lighten skin tone and prevent repigmentation.

The active compounds used in this invention can also be used in combination with sunscreens (UVA or UVB blockers) to prevent repigmentation, to protect against sun or UV-induced skin darkening or to enhance their ability to reduce skin melanin and their skin bleaching action. Such compounds can also be used in combination with retinoic acid or its derivatives or any compounds that interact with retinoic acid receptors and accelerate or enhance the invention's ability to reduce skin melanin and skin bleaching action.

The active compounds used in this invention can also be used in combination with ascorbic acid, its derivatives and ascorbic-acid based products (such as magnesium ascorbate) or other products with an anti-oxidant mechanism (such as resveratrol) which accelerate or enhance their ability to reduce skin melanin and their skin bleaching action.

This invention relates both to methods of lightening or reducing the pigmentation of skin in which the compound of formula I, or pharmaceutically acceptable salt thereof, and one or more of the other active ingredients referred to above are administered together, as part of the same pharmaceutical composition, as well as methods in which they are administered separately as part of an appropriate dose regimen designed to obtain the benefits of the combination therapy. The appropriate dose regimen, the amount of each dose administered, and specific intervals between doses of each active agent will depend upon the specific combination of active agents employed, the condition of the patient being treated, and the nature and severity of the disorder or condition being treated. Such additional active ingredients will generally be administered in amounts less than or equal to those for which they are effective as single topical therapeutic agents. The FDA approved dosages for such active agents that have received FDA approval for administration to humans are publicly available.

The active compounds of the present invention are generally administered in the form of pharmaceutical compositions comprising at least one of the compounds of the formula (I), together with a pharmaceutically acceptable vehicle or diluent. Such compositions are generally formulated in a conventional manner utilizing solid or liquid vehicles or diluents as appropriate for topical administration, in the form of solutions, gels, creams, jellies, pastes, lotions, ointments, salves and the like.

Examples of vehicles for application of the active compounds of this invention include an aqueous or water-alcohol solution, an emulsion of the oil-in-water or water-in-oil type, an emulsified gel, or a two-phase system. Preferably, the compositions according to the invention are in the form of lotions, creams, milks, gels, masks, microspheres or nanospheres, or vesicular dispersions. In the case of vesicular dispersions, the lipids of which the vesicles are made can be of the ionic or nonionic type, or a mixture thereof.

In the depigmenting compositions according to the present invention, the concentration of the active compounds of the invention is generally between 0.01 and 10%, preferably between 0.1 and 10%, relative to the total weight of the composition.

The compositions of this invention can optionally also contain a moistener, a surfactant, keratolytic, an anti-inflammatory agent, a complexing agent, an antioxidant, a preservative, a fragrance, or a sunscreen.

The ability of compounds of the formulae I to inhibit tyrosinase may be determined using any of the following procedures.

1. Tyrosinase (DOPA oxidase) Assay Using Cell Lysate:

Human melanoma cell line, SKMEL 188 (licensed from Memorial Sloan-Kettering, is used in the cell lysate assay and the screen. In the assay, compounds and L-dihydroxyphenylalanine (L-DOPA) (100 µg/ml) are incubated with the cell lysates containing human tyrosinase for 8 hours before the plates are read at 405 nm. Potency of the compounds in DOPA oxidase assay is correlated very well with that in tyrosine hydroxylase assay using 3H-tyrosine as a substrate. 4-Cyclohexylresorcinol, when tested in this assay, exhibited an $IC_{50}$ of 0.3 µM.

2. Melanin Assay in Human Primary Melanocytes:

Compounds are incubated with human primary melanocytes in the presence of α-melanocyte stimulating hormone (α-MSH) for 2–3 days. Cells are then lysed with sodium hydroxide and sodium dodecyl sulfate (SDS) and melanin signals are read at 405 nm. Alternatively, $^{14}C$-DOPA is added to the cells in combination with tyrosinase inhibitors and acid-insoluble $^{14}C$-melanin is quantitated by a scintillation counter. $IC_{50}$'s reflect the inhibitory potency of the compounds in the new melanin synthesis which was stimulated by α-MSH.

3. Tyrosine Kinase Assay (TK):

TK assays can be performed using purified tyrosine kinases domain of c-met, erb-B2, or IGF-r. A specific antibody against phosphorylated tyrosine residue is used in the assay. Colorimetric signals are generated by horse radish peroxidase, which is conjugated to the antibody.

4. Human Skin Equivalent Model:

A mixture of human melanocytes and keratinocytes is grown in an air-liquid interphase. This tissue culture forms a three dimensional structure that histologically and microscopically resembles the human skin epidermis. Test compounds are added on top of the cells to mimic topical drug application. After incubation with the compounds (10 µM) for 3 days, the cells are washed extensively and lysed for DOPA oxidase assay.

5. IL-1 Assay (Interleukin-1 Assay):

An IL-1α ELISA assay (R&D system) can be used to evaluate the effect of compounds on IL-1 secretion in a human skin equivalent model. IL-1α is a pro-inflammatory cytokine and plays a role in UV-induced skin inflammation.

6. In Vivo Study:

Black or dark brown guinea pigs with homogeneous skin color can be used in this study. A solution of the test compound of formula I (5% in ethanol:propylene glycol, 70:30) and the vehicle control are applied to the animals twice daily, 5 days per week for 4–8 weeks. Using this assay, depigmentation of skin was visualized using 5% 4-cyclohexylresorcinol or 5% 4-cyclopentylresorcinol as the test compound.

The present invention is illustrated by the following examples. It will be understood, however, that the invention is not limited to the specific details of these examples. Melting points are uncorrected. Proton nuclear magnetic resonance spectra ($^1H$ NMR) were measured for solutions in $d_6$-DMSO and peak positions are expressed in parts per million (ppm) downfield from tetramethylsilane (TMS). The peak shapes are denoted as follows: s, singlet; d, doublet; t, triplet; q, quartet, m, multiplet, b, broad.

The following examples are illustrative only, and are not intended to limit the scope of the present invention.

EXAMPLES

Example 1

4-Cyclohexylresorcinol

Resorcinol (2.2 g, 20 mmol) and cyclohexanol (6.33 ml, 6 g, 60 mmol) were suspended in 85% polyphosphoric acid (8 ml). The mixture was heated to 125° C. for 24 hours, after which time TLC appeared to show complete consumption of the starting materials. On cooling the mixture was partitioned between water (50 ml) and diethyl ether (50 ml). The aqueous layer was discarded, and the organic portion extracted with sodium hydroxide solution (2×50 ml, 2M).

The base extract was washed with ether (3×50 ml), and then acidified with aqueous hydrochloric acid (120 ml, 2M). The organic components were then extracted into diethyl ether (2×50 ml), dried (magnesium sulfate), filtered and the solvent removed under reduced pressure. The resulting brown oil was then chromatographed on silica gel, eluting with ethyl acetate/petroleum ether (bp 60–80° C.) 1:2 to give the desired product as an off-white solid (1.7 g, 44%).

$^1$H NMR (250 MHz, d$_6$-DMSO): δ 1.13–1.34 (5H, m); 1.65–1.71 (5H, m); 2.67–2.75 (1H, m); 6.11 (1H, dd J=8.3, 2.4 Hz); 6.22 (1H, d, J=2.4 Hz); 6.79 (1H, d, J=8.3 Hz); 8.90 (1H, s); 9.00 (1H, s).

M/Z (ES-ve) gives 191.5 (M-H).

The following compounds were prepared in a similar manner:

Example 2

4-Cyclopentylresorcinol

From cyclopentanol as a white solid $^1$H NMR (250 MHz, d$_6$-DMSO): d 1.34–1.75 (6H, m); 1.78–1.88 (2H, m); 3.06 (1H, quint, J=9.5 Hz); 6.12 (1H, dd, J=2.4, 8.2 Hz); 6.22 (1H, d, J=2.4 Hz); 6.83 (1H, d, J=8.3 Hz); 8.91 (1H, s); 9.01 (1H, s).

M/Z (ES-ve) gives 177.5 (M-H).

Example 3

4-(1-Methyl-1-cyclopentyl)resorcinol

From 1-methylcyclopentanol as a solid.

$^1$H NMR (400 MHz, CDCl$_3$-MeOH): d 1.31 (3H, s); 1.74–1.89 (4H, m); 1.94–2.03 (4H, m); 6.33–6.34 (1H, m); 6.39 (1H, dd, J=2.5, 8.4 Hz); 7.10 (1H, m).

M/Z (ES-ve) gives 191.6 (M-H).

Example 4

4-(1-Methyl-1-cyclohexyl)resorcinol

From 1-methylcyclohexanol as an orange oil. Data reported for a 1:1 mixture of conformers.

$^1$H NMR (250 MHz, d$_6$-DMSO); d 1.20–1.80 (9H, m); 1.97 (3H, s); 2.60–3.00 (1H, m); 6.10–6.14 (1H, m); 6.22–6.70 (1H, m); 6.67–6.85 (1H, m); 8.89–8.90 (1H, m); 8.98–9.02 (1H, m).

M/Z (ES-ve) gives 411.6 (2M-H).

Example 5

4-Cycloheptylresorcinol.

From cycloheptanol as an orange oil. Data reported for a 1:1 mixture of conformers.

$^1$H NMR (250 MHz, d$_6$-DMSO): d 1.30–1.80 (12H, m); 2.60–2.90 (1H, m); 6.08–6.13 (1H, m); 6.20–6.22 (1H, m); 6.78–6.88 (1H, m); 8.86–8.87 (1H, m); 8.89–8.98 (1H, m).

M/Z (ES-ve) gives 205.5 (M-H).

Example 6

4-Cyclooctylresorcinol

From cyclooctanol as an orange oil. Data reported for a 1:1 mixture of conformers.

$^1$H NMR (250 MHz, d$_6$-DMSO): d 1.20–1.80 (14H, m); 2.68–3.00 (1H, m); 6.09–6.15 (1H, m); 6.21–6.23 (1H, m); 6.73–6.84 (1H, m); 8.80–8.83 (1H, m); 8.90–9.00 (1H, m).

M/Z (ES-ve) gives 219.6 (M-H).

Example 7

In Vivo Test Data

In vivo experiments were carried out to determine the depigmenting effects of 4-cyclohexylresorcinol and 4-cyclopentylresorcinol using the assay described above (in vivo study). Thus, 5% 4-cyclohexylresorcinol and 5% 4-cyclopentylresorcinol, each in ethanol:propylene glycol (70:30), were administered separately to the ears of black guinea pigs. Depigmentation was determined by subtracting the light reflectance of untreated ears from the light reflectance of treated ears. As shown by the data in the Table below, both test compositions reduced pigmentation in treated ears starting 3 weeks after initial treatment. The depigmentation effect was reversible, and repigmentation partially resumed one week after ceasing treatment.

TABLE

Depigmentation Effect Of Selected Compounds[a]

| Animal | 3-week | 6-week | 8.5 week | 1 week post-treatment |
|---|---|---|---|---|
| 4-cyclohexylresorcinol | | | | |
| 1A | 13 | 8 | 6 | * |
| 1B | 0 | 0 | 7 | 1 |
| 1C | 14 | 14 | 19 | * |
| 1D | 3 | 7 | 7 | 0 |
| 4-cyclopentylresorcinol | | | | |
| 3B | 15 | 12 | 10 | 6 |
| 3C | 9 | 9 | 18 | * |
| 3D | 4 | 9 | 7 | * |

[a]Depigmentation was determined by Δ light reflectance, which is calculated as (light reflectance of treated ear) − (light reflectance of untreated ear). Positive value indicates depigmentation effect.
*euthanized All patents, patent applications, and publications cited above are incorporated herein by reference in their entirety.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

What is claimed is:

1. A topical pharmaceutical composition for lightening skin or reducing the pigmentation of skin in a human, comprising an amount of a compound of the formula I,

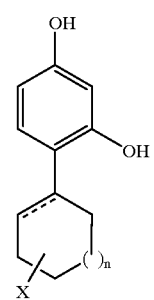

wherein X is hydrogen; OR$^1$, wherein R$^1$ represents hydrogen, (C$_1$–C$_6$)alkyl or aryl-(C$_1$–C$_6$)alkyl; OCOR$^2$ wherein R² represents (C₁–C₆)alkyl, aryl-(C₁–C₆)alkyl or phenyl; halogen; (C₁–C₆)alkyl; aryl-(C₁–C₆)alkyl; SR³ wherein R³ represents hydrogen, (C₁–C₆)alkyl, or aryl-(C₁–C₆)alkyl; or NHR¹ wherein R¹ is defined as above;

n is 0; and the dashed line represents an optional double bond;

or a pharmaceutically acceptable salt thereof, that is effective in lightening skin or reducing the pigmentation of skin, and a pharmaceutically acceptable carrier.

2. The topical pharmaceutical composition of claim 1, wherein the compound of formula I is 4-cyclopentylresorcinol.

3. The composition of claim 2, which is in the form of a water-alcohol solution, an oil-in-water emulsion, a water-in-oil emulsion, an emulsified gel, or a two-phase system.

4. The composition of claim 2, which is in the form of a lotion, cream, milk, gel, jelly, paste, ointment, salve, mask, microspheres, nanospheres, or a vesicular dispersion.

5. A composition according to claim 1, which further comprises a sunscreen.

6. A composition according to claim 1, further comprising resveratrol or another active agent that is an anti-oxidant.

7. A composition according to claim 1, further comprising retinoic acid or a derivative of retinoic acid.

8. A composition according to claim 1, further comprising glycolic acid, trichloroacetic acid or another skin peeling agent.

9. A composition according to claim 1 in the form of a lotion, cream or ointment.

10. The composition of claim 1, which is in the form of a water-alcohol solution, an oil-in-water emulsion, a water-in-oil emulsion, an emulsified gel, or a two-phase system.

11. The composition of claim 1, which is in the form of a lotion, cream, milk, gel, jelly, paste, ointment, salve, mask, microspheres, nanospheres, or a vesicular dispersion.

12. The composition of claim 1, wherein the amount of the compound of formula I is a tyrosinase-inhibiting effective amount.

13. A method of lightening skin or reducing the pigmentation of skin in a human, in need of said treatment comprising administering to said human an amount of a compound of the formula I,

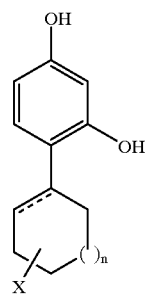

wherein X is hydrogen; OR¹, wherein R¹ represents hydrogen, (C₁–C₆)alkyl or aryl-(C₁–C₆)alkyl; OCOR² wherein R² represents (C₁–C₆)alkyl, aryl-(C₁–C₆)alkyl or phenyl; halogen; (C₁–C₆)alkyl; aryl-(C₁–C₆)alkyl; SR³ wherein R³ represents hydrogen, (C₁–C₆)alkyl, or aryl-(C₁–C₆)alkyl; or NHR¹ wherein R¹ is defined as above;

n is 0 to 3; and the dashed line represents an optional double bond;

or a pharmaceutically acceptable salt thereof, that is effective in lightening skin or reducing the pigmentation of skin.

14. The method of claim 13, wherein the compound of formula I is 4-cyclohexylresorcinol.

15. The method of claim 13, wherein the compound of formula I is 4-cyclopentylresorcinol.

16. The method of claim 15, wherein the compound of formula I is formulated in a water-alcohol solution, an oil-in-water emulsion, a water-in-oil emulsion, an emulsified gel, or a two-phase system.

17. The method of claim 15 wherein the compound of formula I is formulated in a lotion, cream, milk, gel, jelly, paste, ointment, salve, mask, microspheres, nanospheres, or a vesicular dispersion.

18. The method of claim 13, wherein the compound of formula I is formulated in a water-alcohol solution, an oil-in-water emulsion, a water-in-oil emulsion, an emulsified gel, or a two-phase system.

19. The method of claim 13, wherein the compound of formula I is formulated in a lotion, cream, milk, gel, jelly, paste, ointment, salve, mask, microspheres, nanospheres, or a vesicular dispersion.

20. The method of claim 13, wherein the amount of the compound of formula I is a tyrosinase-inhibiting effective amount.

21. A method of inhibiting tyrosinase in a human, in need of said treatment comprising administering to said mammal a tyrosinase inhibiting effective amount of a compound of the formula I,

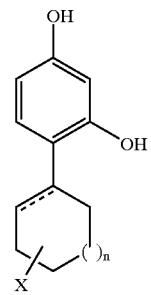

wherein X is hydrogen; OR¹, wherein R¹ represents hydrogen, (C₁–C₆)alkyl or aryl-(C₁–C₆)alkyl; OCOR² wherein R² represents (C₁–C₆)alkyl, aryl-(C₁–C₆)alkyl or phenyl; halogen; (C₁–C₆)alkyl; aryl-(C₁–C₆)alkyl; SR³ wherein R³ represents hydrogen, (C₁–C₆)alkyl, or aryl-(C₁–C₆)alkyl; or NHR¹ wherein R¹ is defined as above;

n is 0 to 3; and the dashed line represents an optional double bond;

or a pharmaceutically acceptable salt thereof.

22. The method of claim 21, wherein the compound of formula I is 4-cyclohexylresorcinol.

23. The method of claim 21, wherein the compound of formula I is 4-cyclopentylresorcinol.

24. The method of claim 23, wherein the compound of formula I is formulated in a water-alcohol solution, an oil-in-water emulsion, a water-in-oil emulsion, an emulsified gel, or a two-phase system.

25. The method of claim 23, wherein the compound of formula I is formulated in a lotion, cream, milk, gel, jelly, paste, ointment, salve, mask, microspheres, nanospheres, or a vesicular dispersion.

26. The method of claim 21, wherein the compound of formula I is formulated in a water-alcohol solution, an oil-in-water emulsion, a water-in-oil emulsion, an emulsified gel, or a two-phase system.

27. The method of claim 21, wherein the compound of formula I is formulated in a lotion, cream, milk, gel, jelly, paste, ointment, salve, mask, microspheres, nanospheres, or a vesicular dispersion.

28. A method of treating an inflammatory disorder in a human, in need of said treatment comprising administering to said human an amount of a compound of the formula I,

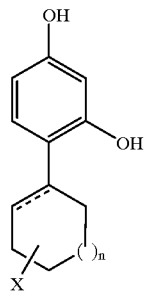

I wherein X is hydrogen; $OR^1$, wherein $R^1$ represents hydrogen, $(C_1-C_6)$alkyl or aryl-$(C_1-C_6)$alkyl; $OCOR^2$ wherein $R^2$ represents $(C_1-C_6)$alkyl, aryl-$(C_1-C_6)$alkyl or phenyl; halogen; $(C_1-C_6)$alkyl; aryl-$(C_1-C_6)$alkyl; $SR^3$ wherein $R^3$ represents hydrogen, $(C_1-C_6)$alkyl, or aryl-$(C_1-C_6)$alkyl; or $NHR^1$ wherein $R^1$ is defined as above;

n is 0 to 3; and the dashed line represents an optional double bond;

or a pharmaceutically acceptable salt thereof, that is effective in treating such disorder.

29. The method of claim 28, wherein the compound of formula I is 4-cyclohexylresorcinol.

30. The method of claim 28, wherein the compound of formula I is 4-cyclopentylresorcinol.

31. A method of lightening skin or reducing the pigmentation of skin in a human, comprising administering to said human an amount of a compound of formula I,

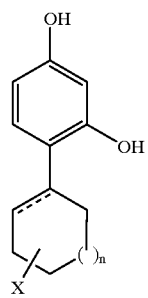

I wherein X is hydrogen; $OR^1$, wherein $R^1$ represents hydrogen, $(C_1-C_6)$alkyl or aryl-$(C_1-C_6)$alkyl; $OCOR^2$ wherein $R^2$ represents $(C_1-C_6)$alkyl, aryl-$(C_1-C_6)$alkyl or phenyl; halogen; $(C_1-C_6)$alkyl; aryl-$(C_1-C_6)$alkyl; $SR^3$ wherein $R^3$ represents hydrogen, $(C_1-C_6)$alkyl, or aryl-$(C_1-C_6)$alkyl; or $NHR^1$ wherein $R^1$ is defined as above;

n is 0;

and the dashed line represents an optional double bond;

or a pharmaceutically acceptable salt thereof;

which amount of the compound of formula I or pharmaceutically acceptable salt thereof is effective in lightening skin or reducing the pigmentation of skin in said human.

32. The method of claim 31, wherein the compound of formula I is 4-cyclopentylresorcinol.

33. The method of claim 31, wherein the compound of formula I or pharmaceutically acceptable salt thereof is formulated in a water-alcohol solution, an oil-in-water emulsion, a water-in-oil emulsion, an emulsified gel, or a two-phase system.

34. The method of claim 31, wherein the compound of formula I or pharmaceutically acceptable salt thereof is formulated in a lotion, cream, milk, gel, jelly, paste, ointment, salve, mask, microspheres, nanospheres, or a vesicular dispersion.

35. The method of claim 31, wherein the amount of the compound of formula I is a tyrosinase-inhibiting effective amount.

* * * * *